(12) United States Patent
Alonso et al.

(10) Patent No.: US 9,398,923 B2
(45) Date of Patent: Jul. 26, 2016

(54) SEALING MEANS FOR THE SEALING OF AN INTRODUCTION FACILITY FOR A MEDICAL INSTRUMENT

(71) Applicant: Karl Storz GmbH & Co. KG, Tuttlingen (DE)

(72) Inventors: Jose Ramon Alonso, Munich (DE); Uwe Bacher, Tuttlingen (DE); Martin Oberlaender, Engen (DE); Michael Sauer, Tuttlingen (DE); Sebastian Wagner, Bretten (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 764 days.

(21) Appl. No.: 13/714,137

(22) Filed: Dec. 13, 2012

(65) Prior Publication Data

US 2013/0150792 A1    Jun. 13, 2013

(30) Foreign Application Priority Data

Dec. 13, 2011    (DE) .......................... 10 2011 088 337

(51) Int. Cl.
*A61B 17/34*    (2006.01)
*A61M 39/06*    (2006.01)
(Continued)

(52) U.S. Cl.
CPC ......... *A61B 17/3417* (2013.01); *A61B 17/3462* (2013.01); *A61M 39/06* (2013.01);
(Continued)

(58) Field of Classification Search
CPC . A61M 39/00; A61M 39/06; A61M 39/0606; A61M 39/0613; A61M 39/22; A61M 39/24; A61M 39/2426; A61M 39/2433; A61M 39/244; A61M 39/2446; A61M 39/246; A61M 39/26; A61M 39/0247; A61M 2039/027; A61M 2039/062; A61M 2039/0626; A61M 2039/0633; A61M 2039/064; A61M 2039/0646; A61M 2039/0653; A61M 2039/066; A61M 2039/0666; A61M 2039/068; A61M 2039/0686; A61B 17/3417; A61B 17/3462; A61B 17/3498; A61B 2017/3419
USPC ........................... 604/167.01, 167.03, 167.04
See application file for complete search history.

(56) References Cited

U.S. PATENT DOCUMENTS

| 4,430,081 A | 2/1984 | Timmermans |
| 4,655,752 A | 4/1987 | Honkanen et al. |

(Continued)

FOREIGN PATENT DOCUMENTS

| DE | 4127628 C1 | 7/1992 |
| DE | 29701600 U1 | 7/1997 |

(Continued)

OTHER PUBLICATIONS

European Search Report Application No. EP 12 19 5932 Completed: Feb. 25, 2013; Mailing Date: Mar. 5, 2013 10 pages.

*Primary Examiner* — Theodore Stigell
*Assistant Examiner* — Amber Stiles
(74) *Attorney, Agent, or Firm* — Whitmyer IP Group LLC

(57) ABSTRACT

A sealing means for sealing an introduction facility for a medical instrument includes a first sealing membrane of an elastic material with a first slit and a second sealing membrane of an elastic material with a second slit. The first sealing membrane and the second sealing membrane abut laminarily on each other. The first sealing membrane and the second sealing membrane are arranged such that the first slit and the second slit are not parallel with each other. Each of the first slit and the second slit is unbranched.

15 Claims, 6 Drawing Sheets

(51) Int. Cl.
*A61B 17/00* (2006.01)
*A61M 39/02* (2006.01)

(52) U.S. Cl.
CPC ... *A61B17/3498* (2013.01); *A61B 2017/00862* (2013.01); *A61M 39/0247* (2013.01); *A61M 2039/064* (2013.01); *A61M 2039/0626* (2013.01); *A61M 2039/0633* (2013.01); *A61M 2039/0686* (2013.01)

(56) References Cited

U.S. PATENT DOCUMENTS

| | | | |
|---|---|---|---|
| 4,857,062 A | 8/1989 | Russell | |
| 5,366,446 A | 11/1994 | Tal et al. | |
| 5,727,770 A | 3/1998 | Dennis | |
| 6,352,520 B1* | 3/2002 | Miyazaki | A61M 39/045 604/167.03 |
| 6,379,372 B1 | 4/2002 | Dehdashtian et al. | |
| 6,551,283 B1* | 4/2003 | Guo | A61M 39/06 251/149.1 |
| 2004/0267185 A1* | 12/2004 | Weaver | A61M 1/3653 604/6.16 |
| 2006/0135977 A1 | 6/2006 | Thompson et al. | |
| 2008/0086074 A1 | 4/2008 | Taylor et al. | |
| 2010/0280456 A1* | 11/2010 | Nijland | A61M 39/06 604/167.03 |

FOREIGN PATENT DOCUMENTS

| | | |
|---|---|---|
| DE | 69329286 T2 | 12/2000 |
| DE | 60105973 T2 | 10/2005 |
| EP | 0536549 A1 | 4/1993 |
| EP | 0630660 A1 | 12/1994 |
| EP | 0746359 B1 | 12/1996 |
| EP | 1269925 A1 | 1/2003 |
| EP | 1350476 A1 | 10/2003 |
| EP | 1459688 A1 | 9/2004 |
| EP | 1671598 A1 | 6/2006 |
| FR | 2694181 A1 | 2/1994 |
| WO | 9112838 A1 | 9/1991 |
| WO | 9301850 A1 | 2/1993 |
| WO | 9401149 A1 | 1/1994 |
| WO | 9832484 A1 | 7/1998 |
| WO | 0154763 A2 | 8/2001 |
| WO | 2006118748 A1 | 11/2006 |
| WO | 2007148959 A1 | 12/2007 |
| WO | 2010045702 A1 | 4/2010 |
| WO | 2011060192 A1 | 5/2011 |

* cited by examiner

SEALING MEANS FOR THE SEALING OF AN INTRODUCTION FACILITY FOR A MEDICAL INSTRUMENT

FIELD OF THE INVENTION

The present invention refers to sealing means for the sealing of an introduction facility for a medical instrument, in particular for the sealing of a trocar through which an endoscope and/or other medical instruments can be introduced into a natural or artificial cavity in the course of a microinvasive medical intervention, and for the sealing of a working channel of an endoscope.

BACKGROUND OF THE INVENTION

Laparoscopy is one example of microinvasive medial methods. An artificial port to the abdominal cavity of a patient through the abdominal wall of the patient is formed by means of a trocar. An endoscope and/or further medical instruments (for instance forceps, scissors, acutenaculums) can be introduced into the abdominal cavity through the lumen of a trocar's cannula remaining in the abdominal wall during the laparoscopic intervention. During laparoscopy, the abdominal cavity is filled with carbon dioxide or another gas in order to form a pneumoperitoneum, a cavity facilitating the medical intervention. Without specific measures, the gas would leak through the lumen of the trocar's cannula. Therefore, numerous approaches have been developed for sealing the lumen of the trocar's cannula as tight as possible, both in an empty state and when an instrument is introduced. Partly similar problems can arise at a working channel of an endoscope or when a catheter is introduced into a blood vessel. In the latter case, however, leakage of blood rather than gas needs to be prevented.

In U.S. Pat. No. 4,857,062, a valve for the introduction of a catheter to an artery is described. For sealing purposes, a duck bill shaped first element and a second flexible element are provided, wherein the second flexible element is compressed in order to form a fluid tight sealing with a catheter. Both elements are arranged fixedly an in series in a housing.

In WO 93/01850 A1, a lever actuated sealing for a trocar is described. An elastomeric septum with an orifice is stretched by means of several levers, whereby the orifice is expanded.

In U.S. Pat. No. 5,366,446, an introducer assembly for use on the skin of a patient is described, the introducer assembly being provided for the introduction of tubes with different outer diameters. The assembly comprises a membrane of a pierceable elastomeric material in the center of a bellows.

In EP 0 630 660 A1, a sealing assembly for accommodating of a surgical instrument is described. The sealing assembly comprises a duck bill seal or an arrangement of a plurality of seal members, a part of which is slotted in star-shape and which partially overlap each other and a part of which is shaped conically.

In EP 0 746 359 B1, a catheter check valve is described. For sealing purposes, a rubber seal with an orifice and a duck bill valve with a straight slit distal of the rubber sealing are provided.

In WO 2010/045702 A1, a disposable sealing for a trocar is described. The disposable sealing is approximately cup-shaped with cuts crossing each other at the bottom.

In U.S. Pat. No. 4,430,081, a cannula for use with angiography catheters is described. A first sealing with a slit, a second sealing with a hole and a third sealing with a flapper are provided adjacent to each other for sealing against ingression of air or leakage of blood from a blood vessel.

In WO 91/12838 A1, an infusion port with several elastic discs in series is provided, each of the discs comprising a circular orifice or star-shaped slits, one disc rotated with respect to the other.

In EP 0 536 459 A1, a trocar sleeve for the introduction of a medical instrument is described. A sealing assembly for sealing an axial passage and for sealing a hollow shaft both when an instrument is introduced and when no instrument is introduced comprises one or more septums of elastic material with cross-shaped slits staggered with respect to each other.

In WO 94/01149 A1 and DE 693 29 286 T2, a valve for an introduction assembly is described. A body of silicone or of another elastomeric material comprises a cylindrical wall inclosing a bore. One end of the cylindrical wall and of the bore is closed by a wall with a central orifice. The other end of the wall and of the bore is closed by two inclined plates with a slit there between.

In WO 98/32484 A1, an instrument for introducing catheters with a hemostatic valve is described. A sealing element comprises two perforated supporting discs, wherein a sealing disc of soft elastic foam plastic with radial slits is provided between the supporting discs.

In EP 1 269 925 A1, an access cannula for endoscopic surgery is described. A double disc valve comprises two discs with three-beam star-shaped slits each, wherein the slits of both discs are arranged staggered with respect to each other.

In EP 1 350 476 A1, a trocar sleeve with a valve is described. The valve comprises an introduction region with wall sections which converge towards one another in the distal direction and which are provided as sloping surfaces, and sealing lips abutting one another elastically.

In DE 297 01 600 U1 the valve mechanism for medical applications is described. Two similar valve discs with a centrally located slit each are arranged in a casing and form an angle in the range of 60 degree to 90 degree.

In DE 601 05 973 T2 a hemostasis valve is described comprising proximal valve sealing with a slit and a distal valve sealing with a slit. A positioning protrusion restricts the relative rotation of the valve sealings.

In US 2006/0135977 A1 a trocar sealing structure with two conical sealing sections is described.

Each of the sealing means described provides specific advantages and disadvantages. For many applications, no satisfactory solutions have been found or, at least, further improvements are desired. This holds particularly with regard to the fact that sealing means shall fulfill numerous requirements simultaneously. In particular, sealing means are required to be fluid tight, robust, reusable and for this purpose in particular autoclavable, to resist axial motion of a medical instrument as little as possible, to facilitate lever type manipulation, or tilting, of a medical instrument introduced into the sealing means and at the same time to stay fluid tight, and to allow cost effective production. Furthermore, sealing means are required to be cleanable with little effort, to provide a compact construction, in particular a short installation length (metered from the proximal to the distal end of the sealing means), and to be suitable for medical instruments with different cross sections. Furthermore, it is required that medical instruments with cross sections varying in longitudinal direction, in particular with undercuts, steps, offsets, and soft tissue can pass the sealing means in the direction from distal to proximal as well, thereby not getting stuck or caught in another way by the sealing means.

SUMMARY OF THE INVENTION

It is an object of the present invention to provide improved sealing means, in particular fulfilling the enumerated requirements and expectations in balanced proportion.

This object is solved by the subject matters of the independent claims.

Further aspects are given in the dependent claims.

Embodiments of the present invention are based on the idea to provide, at a sealing means, two sealing membranes abutting on each other, each sealing membranes with a straight or at least unbranched slit. In particular, the slits of the two sealing membranes are arranged forming an angle of around 90 degree to each other. This configuration of the sealing means can facilitate a sealing function both without a medical instrument in the sealing means and with a medical instrument introduced into the sealing means, and for a large variety of diameters or cross sections of medical instruments.

A sealing means for sealing an introduction facility for a medical instrument comprises a first sealing membrane of an elastic material, with a first slit, and a second sealing membrane of an elastic material, with a second slit, the first sealing membrane and the second sealing membrane laminarily abutting on each other, the first sealing membrane and the second sealing membrane being arranged such that the first slit and the second slit are not parallel with each other, each of the first slit and the second slit being unbranched.

In particular, the sealing means is a sealing means for a trocar or for a trocar's cannula forming a port to a cavity during a microinvasive intervention. As an alternative, the sealing means is provided and configured for a working channel of an endoscope or for another medical device into which medical device a medical instrument can be introduced and which medical device is required to be closed fluid tightly with and without the medical instrument.

In particular, the sealing means is provided and configured to be attached removably to the proximal end of a trocar or of a working channel of an endoscope or of another medical device. In particular, for this purpose, the sealing means comprises an attachment region with an elastic flange or another surface region facilitating a positive-locking mechanic connection with a correspondingly shaped surface region of a medical device.

In particular, the first sealing membrane and the second sealing membrane are made of silicone or a similar elastic, biocompatible and autoclavable material. Each of the first slit and the second slit are formed or defined by two sealing lips of the corresponding sealing membrane, wherein, in a stress-free state of the sealing membrane, the sealing lips abut on each other or, at the most, provide a very small distance. In particular, the first sealing membrane and the second sealing membrane completely or almost completely abut on each other. Each of the slits in the sealing membranes is in so far unbranched as it is in particular not cruciform or star-shaped.

The sealing means can comprise a third sealing membrane. In particular, the third sealing membrane directly and entirely abuts on the first sealing membrane or on the second sealing membrane. Furthermore, the sealing means can comprise a fourth sealing membrane or further sealing membranes which can, together with the first sealing membrane, the second sealing membrane and the third sealing membrane, form a stack. In particular, each sealing membrane directly and entirely abuts on the adjacent sealing membrane or on the adjacent sealing membranes.

The sealing lips being, in a relaxed state, straight or slightly arcuate and forming an unbranched slit can abut on two opposite regions of a circumference of a medical instrument but, as a rule, not on the entire circumference of a medical instrument. Sealing lips forming two staggered slits in two sealing membranes can, together and if configured to be sufficiently elastic, abut on the entire circumference of a medical instrument. When both sealing membranes abut on each other, the four sealing lips forming the two slits in the two sealing membranes can, together, abut on the entire circumference of a medical instrument and, in this way, form a largely or entirely fluid tight arrangement.

Conventional sealing means with star-shaped slits provide this characteristic to a lesser degree. Star-shaped slits may be intuitively obvious (and a multiplicity of these are described in the state of the art summarized above) since the tongue-shaped regions of the sealing membrane between the radial sections of the star-shaped slits are primarily bent elastically and are expanded or sheared to a minor degree only when a medical instrument is introduced. In fact, the usage of one unbranched slit in each sealing membrane may require a higher elasticity regarding expansion and shearing, but, concurrently, can facilitate a degree of fluid tightness unobtainable with star-shaped slits.

When the direction of motion of a medical instrument in the sealing means is reversed (introduction/extraction) two unbranched slits arranged rotated with respect to each other in two sealing membranes abutting on each other can be advantageous, too. In particular, depending on a friction between the sealing lips and the medical instrument, folding of the sealing lips can proceed particularly smoothly and, thereby, particularly, advantageous with respect to the sealing function, or can be omitted entirely.

Furthermore, the sealing means can facilitate a radial adjustment to small cross sections of medical instruments to be introduced and can be suitable for a large range of diameters or numerous different cross sections of medical instruments. Medical instruments providing a cross section which is larger at the distal end than proximal the distal end and/or providing undercuts and tissue can be extracted from the sealing means more easily and with a lower risk of complication. Unlike many conventional sealing means, the sealing means described herein do not or to a minor degree provide the property of a "mousetrap" for medical instruments and other objects with not entirely cylindrical shape.

Sealing means described herein can concurrently provide the function of fluid tight closure for a medical device when no medical instrument is introduced and the function of a fluid tight sealing when a medical instrument is introduced. Simultaneously, the sealing means can provide a comparatively short overall length and a simple construction of few components. In particular, the sealing means comprises only two components.

In a sealing means as described herein, in particular at least one of the thickness of the first sealing membrane decreases continuously or discontinuously towards the first slit and the thickness of the second sealing membrane decreases continuously or discontinuously towards the second slit.

In sealing means as described herein, in particular at least one of in regions adjacent on both sides of the first slit the thickness of the first sealing membrane decreases towards the first slit in wedge-shape and in regions adjacent on both sides of the second slit the thickness of the second sealing membrane decreases towards the second slit in wedge-shape.

In particular, each of the regions adjacent to the slits, in which the thickness of the first sealing membrane or the thickness of the second sealing membrane decreases in wedge-shape, respectively, is strip-shaped or rectangular. In particular, the minimum thickness of the first sealing membrane or of the second sealing membrane, respectively, proximate the corresponding slit or the edge of the corresponding sealing lip, respectively, is 0.2 mm or less. In particular, the angle between the sealing membrane's proximal and distal surfaces converging towards the slit is 30 degree or less.

The sealing membranes getting thin towards the respective slits, or the described discontinuous, continuous or tapered reduction of the thickness of the sealing membranes, facilitates an adjustment of the elasticity of the sealing lips formed by the sealing membranes within a wide range. By means of the described configuration of the sealing lips and the selection of the material, in particular of the material's elasticity and hardness, it can be achieved that each of the sealing lips abuts on the circumference of a medical instrument in a region of more than 90 degree for medical instruments with cross sections and diameters within a comparatively large range. When the relative arrangement of the slits in the two sealing membranes is suitable, and since the sealing membranes are configured to abut on each other two-dimensionally, both sealing membranes together can abut on the entire circumference of the medical instrument without or substantially without a gap.

Furthermore, the discontinuous or continuous and in particular wedge-shaped decrease of the thickness of the sealing membranes towards the slits and the resulting increase of the elasticity of the sealing membranes towards the slits can reduce the risk of demolition or damage to the sealing membranes, in particular by acute or sharp-edged medical instruments and other objects.

For a further increase of the robustness or for a decrease of the risk of demolition or damage, the sealing means can be reinforced by a coating or by objects of tougher or harder material (for instance polymer, metal or ceramics) in the proximity of the slits.

In sealing means as described herein, in particular each of the length of the first slit and the length of the second slit is at least twice the largest diameter of a section of a medical instrument for which the sealing means is provided.

In particular, the largest diameter of a section of the medical instrument for which the sealing means is provided results from the cross section or the diameter of the lumen of a trocar's cannula for which the sealing means is provided and configured. When the length of the slits is at least twice the largest diameter of said section of a medical device the described sealing effect and in particular the abutting of each single sealing lip in a region of more than 90 degree can be achievable particularly easily.

In sealing means as described herein, each of the first sealing membrane and the second sealing membrane is, in particular, configured such that each sealing lip adjoining a slit abuts on a medical instrument's largest circular cross section for which the sealing means is provided, in a region extending, in a circumferential direction, over at least 90 degree.

As already mentioned above, such configuration of the sealing membranes facilitates that the sealing lips together abut on the entire circumference of a medical instrument without or substantially without a gap and, in this way, are sealing fluid tightly.

In particular, a sealing means as described herein comprises a positive-locking connection of the first sealing membrane and the second sealing membrane.

In sealing means as described herein, the first sealing membrane and the second sealing membrane are, in particular, mechanically connected to each other by means of one or more snap-lock connections.

In particular, the first sealing membrane and the second sealing membrane are mechanically connected to each other by means of two snap-lock connections located at opposite sides. As an alternative, the first sealing membrane and the second sealing membrane are mechanically connected to each other by means of three or four snap-lock connections in equal distances.

In particular, each snap-lock connection comprises a latch permanently connected to one of the sealing membranes, wherein the latch can, for instance, engage with a recess or an eye at the other sealing membrane. In particular, each of the latch and the recess, the eye or the other facility corresponding to the latch is located at a frame connected to a corresponding one of the sealing membranes. The frame can comprise a material different from the material of the respective sealing membrane and can be glued, welded or otherwise materially bonded to the respective sealing membrane. In particular, the frame comprises a material more rigid or less elastic than the material of the respective sealing membrane. As an alternative, the frame comprises the same material as the respective sealing membrane. In this case, a larger material thickness in the region of the frame can cause less elasticity of the frame.

In sealing means as described herein, in particular the first sealing membrane and the second sealing membrane are arranged such that the first slit and the second slit form an angle of at least 60 degree or at least 80 degree or form an angle of 90 degree.

In sealing means as described herein, in particular each of the first slit and the second slit is straight or curved wherein the radius of curvature at least equals a length, a width or a diameter of the first sealing membrane or of the second sealing membrane.

In case of curved sealing membranes a slit is called straight when the slit lies in a plane which is, in the center of the slit or at all positions at the slit, orthogonal to the sealing membrane. A straight or merely slightly curved configuration of the slits can facilitate the sealing effect of the sealing means.

In sealing means as described herein, in particular each of the first sealing membrane and the second sealing membrane is dome-shaped at least in a central region.

In particular, each of the first sealing membrane and the second sealing membrane is dome-shaped at least in a circular region the diameter of which corresponds to the length of the first slit or to the length of the second slit. In particular, each of the first sealing membrane and the second sealing membrane is substantially entirely dome-shaped.

In sealing means as described herein, in particular each of the first sealing membrane and the second sealing membrane comprises a spherical surface region adjacent to the slits.

The central region of a membrane is dome-shaped, when the Gaussian curvature is continuously positive. In particular, each dome-shaped region or each spherical surface section provides a circular boundary. A dome-shaped and in particular a spherical configuration of the sealing membranes near the slits can support the described sealing effect. Furthermore, the sealing membranes can be funnel-shaped outside the dome-shaped regions or outside the regions within which they comprise spherical surface sections. The dome-shape and in particular the spherical shape and, if applicable a funnel-shaped or conical configuration can simplify the introduction of a medical instrument into the sealing means. Furthermore, the risk of damaging by pointed or sharp-edged medical instruments can be avoided as the point of the medical instruments, sliding along the slanted surface of the proximal sealing membrane, is led to the slits.

In sealing means as described herein, in particular a first edge profile is provided at the outer boundary of the first sealing membrane and a second edge profile is provided at the outer boundary of the second sealing membrane, the first edge profile and the second edge profile being configured for a positive-locking connection between the first sealing membrane and the second sealing membrane.

In particular, one of the two edge profiles is designed as a flange protruding radially outward, and the other of the two edge profiles is configured as a groove radially open towards the center, wherein the flange and the groove provide corresponding cross sections. Such edge profiles and similar edge profiles facilitate a positive-locking mechanic connection of the sealing membranes which connection can be made and released by elastic deformation of the two sealing membranes. In this way, the sealing means can, with little effort, be disassembled for cleaning and sterilization and reassembled thereafter. Tools are not required. In order to further simplify disassemblage of the sealing means, a tab or another facility can be provided at the outer boundary of one of the two sealing membranes, the tab or other facility facilitating separation of the edge profiles. The disassembling option can facilitate or convey the reusability of the sealing means.

In sealing means as described herein, in particular each of the outer boundary of the first sealing membrane and the outer boundary of the second sealing membrane deviates, at at least one respective position, from circular symmetry in such a way that a predetermined relative orientation of the sealing membranes is given.

For example, a protrusion is provided at the first sealing membrane, and a corresponding recess is provided at the second sealing membrane in such a way that the first sealing membrane and the second sealing membrane can be connected with each other merely in a configuration in which the protrusion is positioned in the recess. By these or similar features, it can be achieved that the slits in the sealing membranes always provide the predetermined relative orientation, in particular that they are arranged at right angles to each other.

In particular, sealing means as described herein comprise at least one of a reinforcement rib at the first sealing membrane and a reinforcement rib at the second sealing membrane.

A reinforcement rib is, in particular, arranged substantially perpendicular (forming an angle of at least 60 degree) to the first slit or to the second slit, respectively, and is, in particular, arranged in the middle of the first slit or of the second slit, respectively. Reinforcement ribs at the first and/or second membrane allow affecting or setting the elastic deformability of the membrane in an advantageous way. Each of the reinforcement ribs can provide a cross section in the shape of a rectangle, a semicircle, a part of an ellipse or in other shape. The cross section of a reinforcement rib can vary along the reinforcement rib. In particular, at both sides of the slit, reinforcement ribs are arranged symmetrically to each other at the sealing membrane. As an alternative, several reinforcement ribs can be arranged at each side of the slit.

In sealing means as described herein, in particular at least one of the first sealing membrane and the second sealing membrane provides a friction reducing coating at at least one side.

A friction reducing coating of the sealing membrane at least near the slits can reduce the forces required for a motion of a medical instrument in the sealing means for overcoming the static and dynamic friction, and, in addition, can impede folding of the sealing lips when the direction of motion is reversed. Furthermore, a reduction of the friction by means of the coating can diminish the risk of destruction or damage to the sealing means, in particular when a pointed or sharp-edged medical instrument is introduced. A coating on the sealing membranes' facing and abutting surfaces can support contact between the sealing lips and a medical instrument introduced into the sealing means and, thereby, the sealing effect. In particular, both (proximal and distal) surfaces of both sealing membranes or all surfaces of the sealing means are coated.

In particular, the reduced friction coating of the sealing means comprises Poly(p-Xylylene), also sold under the Trademark Parylene.

Sealing means as described herein, in particular comprise an attachment region for attachment of the sealing means to a trocar or to another medical device and an elastic wall section shaped like a lateral surface and surrounding the second sealing membrane, the elastic wall section connecting the second sealing membrane to the attachment region, wherein the elasticity of the elastic wall section facilitates a motion of the sealing membranes relative to the attachment region.

In particular, the elastic wall section substantially provides the shape of an annular section of the lateral surface of a circular cylinder or of a cone. The elastic wall section may provide a constant wall thickness or a wall thickness increasing or decreasing from proximal to distal. In particular, a first edge of the elastic wall section is connected to the outer boundary of the second sealing membrane. A second edge of the elastic wall section is connected to the attachment region. In particular, each of the first edge and the second edge of the elastic wall section is circular. In particular, the elastic wall section is formed integral with the second sealing membrane and/or with the attachment region. In particular, the elastic wall section provides the function of a bellows or is part of a bellows.

The elasticity of the elastic wall section can facilitate a motion of the sealing membrane relative to the attachment region, in particular a shift of the sealing membrane in direction perpendicular to the direction of introduction and/or a tiling or pivoting motion of the sealing membrane relative to the attachment region. In this way, the elasticity of the elastic wall section can reduce the resulting forces between the medical instrument and the sealing means, in particular, the sealing lips, in tilting or lever like motion of the medical instrument inside the sealing means. In this way, a sealing effect of the sealing means is promoted and the risk of damage to the sealing means is reduced. Therefore, a reusable design of the sealing means can be expedient and contribute to low life cycle costs.

A trocar comprises sealing means as described herein.

In particular, the trocar, apart from said sealing means, does not provide further sealing means closing the trocar when a medical instrument is introduced into the trocar or closing the trocar without a medical instrument introduced.

BRIEF DESCRIPTION OF THE DRAWINGS

Hereinafter, embodiments are further described with reference to the appended Figures.

DETAILED DESCRIPTION OF THE INVENTION

Figure 1:
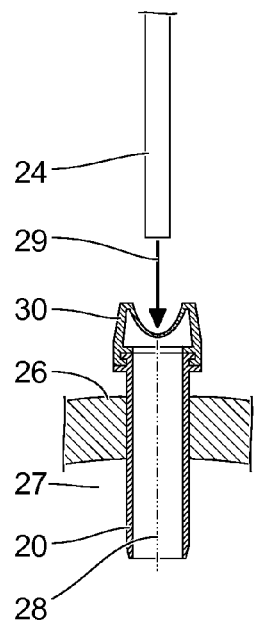
FIG. 1 displays a schematic representation of a trocar with a medical instrument.
Figure 2:
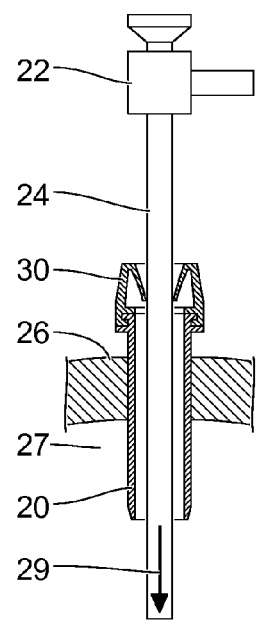
FIG. 2 displays another schematic representation of the trocar and the medical instrument of FIG. 1.

FIGS. 1 and 2 display schematic representations of a section of a trocar 20, or rather a trocar's cannula, inserted in the abdominal wall 26 of a patient. Through the lumen of the trocar 20, one or more medical instruments can be introduced into a cavity 27 beneath the abdominal wall 26 of the patient. The trocar 20, the abdominal wall 26 and the cavity 27 beneath the abdominal wall 26 are represented in a section along a plane comprising a longitudinal axis 28 of the trocar 20. In particular, the trocar 20 provides, at least partially, rotational symmetry with respect to the longitudinal axis 28. The trocar 20 comprises sealing means 30 at the trocar's proximal end outside the cavity 27. Embodiments of the sealing means 30 are described in more detail with reference to FIGS. 3 through 17.

Furthermore, a medical instrument 22 with a shaft 24 is shown in FIGS. 1 and 2. Since the internal structure of the medical instrument 22 and its shaft 24 are not relevant to the trocar's 20 properties described below, merely contours of the medical instrument 22 and of its shaft 24 are represented for the sake of convenience. In FIG. 2, the medical instrument 22 is illustrated exemplarily as an endoscope.

The shaft 24 of the medical instrument 22 can be introduced into the trocar 20 in a direction 29 parallel or substantially parallel to the longitudinal axis 28 of the trocar 20. In FIG. 1, the shaft 24 of the medical instrument 22 is shown before it is introduced into the trocar 20 or rather its lumen, and in FIG. 2 the shaft 24 of the medical instrument 22 is shown after its introduction into the trocar 20 or rather the trocar's 20 lumen. The sealing means 30 fluid tightly closes the trocar's 20 proximal end both when, as shown in FIG. 1, no medical instrument is introduced into the trocar 20 and when, as shown in FIG. 2, a medical instrument 22 is introduced into the trocar 20. Thereby, the sealing means 30 inhibits a leakage of gases or other fluids from the cavity 27 beneath the patient's abdominal wall 26.

Figure 3:
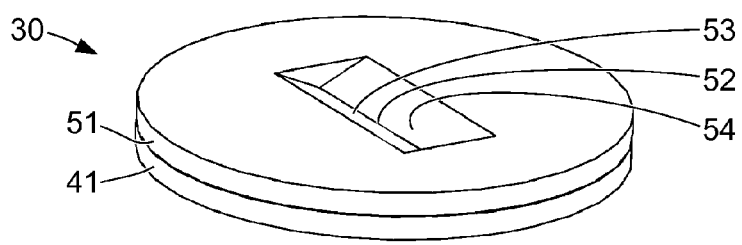
FIG. 3 displays a schematic axonometric representation of sealing means.

FIG. 3 displays a schematic axonometric representation of a simple embodiment of the sealing means 30 with a first sealing membrane 41 and a second sealing membrane 51. In the example shown, each of the first sealing membrane 41 and the second sealing membrane 51 is substantially planar, plate-shaped and circular. Both sealing membranes 41, 51 are in direct contact with each other that it to say a substantially planar surface of the first sealing membrane 41 entirely abuts on a substantially planar surface of the second sealing membrane 51. A straight slit 52 between two sealing lips 53, 54 is located in the center of the second sealing membrane 51. A second slit between two sealing lips invisible in FIG. 3 is located in the center of the first sealing membrane 41.

Figure 4:
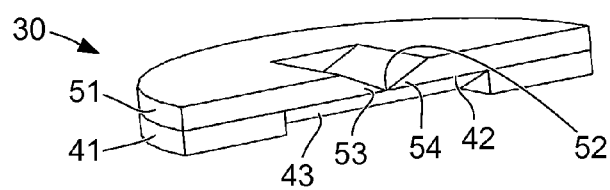
FIG. 4 displays another schematic axonometric representation of the sealing means of FIG. 3.

FIG. 4 displays another schematic axonometric representation of the sealing means 30 of FIG. 3. In contrast to FIG. 3, in FIG. 4 the sealing means 30 is shown in section along a plane comprising the slit 42 in the first sealing membrane 41. The slit 52 in the second sealing membrane 51 is perpendicular to the slit 42 in the first sealing membrane 41 and thus perpendicular to the sectional plane, too.

In the section shown, it can be seen that the second sealing membrane's 51 sealing lips 53, 54 are formed by the second sealing membrane's 51 regions narrowing in wedge-shape towards the slit 52. In other words, in each strip-shaped or rectangular region adjacent to the slit 52, the thickness of the second sealing membrane is a linear or affine-linear function of the distance from the slit 52. The same applies for a sealing lip 43 and another sealing lip not shown in FIG. 4 of the first sealing membrane 41 which form the slit in the first sealing membrane 41. Each of the second sealing membrane's 51 surface abutting on the first sealing membrane 41 and the first sealing membrane's 41 surface abutting on the second sealing membrane 51 is planar so that the sealing membranes 41, 51 are entirely in contact.

Figure 5:
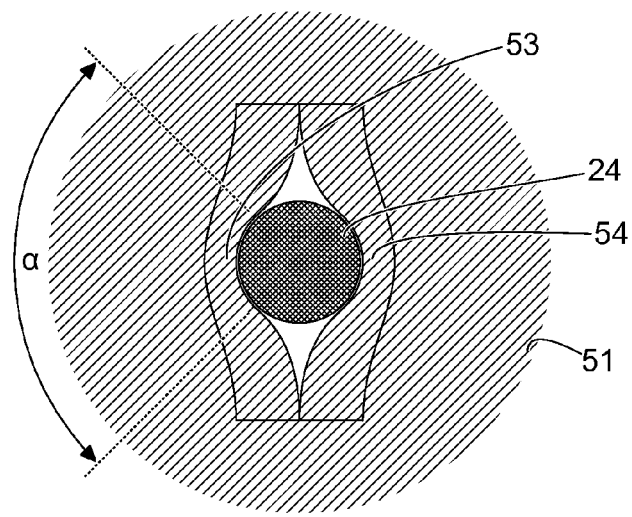
FIG. 5 displays another schematic representation of the sealing membrane of FIGS. 3 and 4.

FIG. 5 displays another schematic representation of the second sealing membrane 51. The plane of projection of FIG. 5 is perpendicular to the longitudinal axis 28 and to the direction of introduction 29 of a trocar's cannula for which the sealing means is provided (confer FIGS. 1 and 2) and parallel to the second sealing membrane's 51 planar surface averted from the viewer and configured to abut on the first sealing membrane not in shown in FIG. 5.

FIG. 5 displays the second sealing membrane 51 together with a medical instrument's shaft 24 shown in section. In FIG. 5 (and in FIG. 6) the hatching of the second sealing membrane does not indicate a sectional area but improves perceptibility of the second sealing membrane 51. The shaft 24 is introduced into the slit between the sealing lips 53, 54 of the second sealing membrane 51. The second sealing membrane 51 and in particular its sealing lips 53, 54 are elastically deformed by the shaft 24.

Each of the sealing lips 53, 54 abuts on the circumference of the shaft 24 of the medical instrument in a region extending over an angle a (alpha). The second sealing membrane 51, in particular the material, the thickness, the width and the length of the second sealing membrane's 51, in a relaxed state, rectangular regions forming the sealing lips 53, 54 and the wedge-shape (wedge angle, or local dependence of thickness) of the regions forming the sealing lips 53, 54, are configured such that the angle α (alpha) is at least 90 degree. The same holds true for the first sealing membrane 41 not displayed in FIG. 5.

Figure 6:
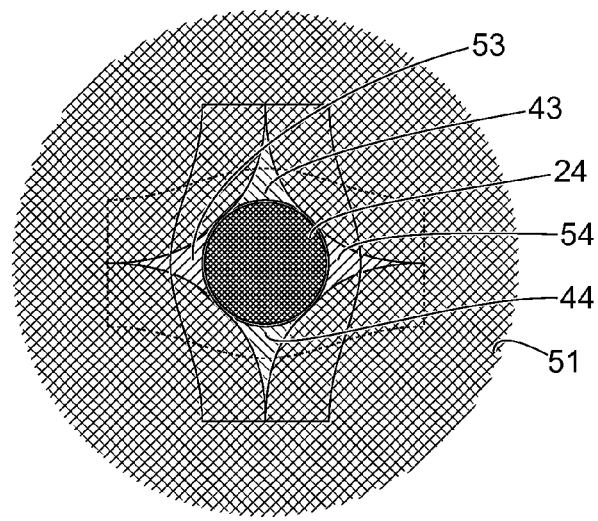
FIG. 6 displays a schematic representation of the sealing membranes of FIGS. 3 and 4.

FIG. 6 displays a schematic representation of both sealing membranes 41, 51, the representation corresponding, with regard to the plane of projection and to the viewing direction, to FIG. 5. The first sealing membrane 41 is located at the second sealing membrane's 51 side averted from the viewer and is, therefore, covered to a large extent by the second sealing membrane 51. However, both sealing membranes 41, 51 can be distinguished by means of their hatchings. The first sealing membrane 41 is hatched from top left to bottom right, the second sealing membrane 51 is hatched from bottom left to top right. Where both sealing membranes 41, 51 cover, or overlap, each other, a narrow spaced cross hatching results.

It can be seen that the sealing lips 43, 44, 53, 54 of the sealing membranes 41, 51 alternately and without a gap abut on the entire circumference of the shaft 24 of the medical instrument. This is caused on the one hand by, as already described above with reference to FIG. 5, each sealing lip 53, 54 of the second sealing membrane 51 and in the same way each sealing lip 43, 44 of the first sealing membrane 41 abutting on the shaft 24 of the medical instrument in a region extending, in a circumferential direction, over at least 90 degree, and on the other hand by the first sealing membrane 41 and the second sealing membrane 51 and the slits formed by the sealing lips 43, 44, 53, 54 being rotated by 90 degree relative to each other.

Figure 7:
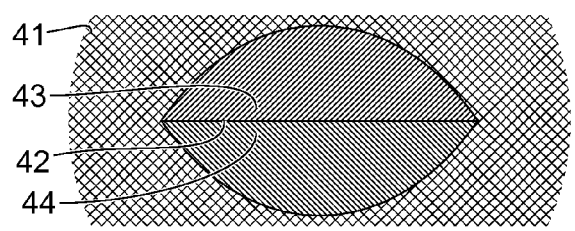
FIG. 7 displays a schematic representation of another sealing membrane.

FIG. 7 shows a schematic representation of another embodiment of a sealing membrane 41 which is, regarding several characteristics, similar to the sealing membranes described above with reference to FIGS. 3 through 6. Regarding the plane of projection, the illustration in FIG. 7 is similar to the illustrations in FIGS. 5 and 6, however, hatching is different. The sealing membrane's 41 region in which the sealing membrane 41 provides a constant thickness is represented by a cross hatching. The sealing membrane's 41 regions forming the sealing lips 43, 44 are represented by a linear hatching from bottom left to top right or from top left to bottom right, respectively.

In the embodiment shown in FIG. 7, the regions forming the sealing lips 43, 44 are not rectangular, as in the sealing membranes illustrated above with reference to FIGS. 3 through 6. Rather, the boundary lines between the regions forming the sealing lips 43, 44 and the ambient region in which the sealing membrane 41 provides a constant thickness is arcuate. In particular, the regions forming the sealing lips 43, 44 are wider in the center of the slit 42 and narrowing towards the ends of the slit 42.

Along the slit 42 (i.e. in FIG. 7 from left to right), the wedge-shape of the region forming the sealing lips 43, 44 can be constant so that the thickness of the sealing membrane 41 is constant along the entire slit 42 and is the same function of the distance from the slit 42 everywhere. The outcome of this is a step between the region forming the sealing lips 43, 44 and the ambient constant thickness region of the sealing membrane 41, which step provides a height varying as a function of the position.

As an alternative, the wedge angle of the wedge-shape of the regions forming the sealing lips 43, 44 is the same everywhere, and, immediately at the slit 42, the thickness of the sealing lips 43, 44 varies along the slit 42 in such a way that there is a stepless continuity between the regions forming the sealing lips 43, 44 and the ambient constant thickness region of the sealing membrane 41. As a further alternative, the wedge-shape (in particular the wedge angle) of the regions forming the sealing lips 43, 44 varies along the slit 42 such that the thickness of the sealing lips 43, 44 at the slits 42 is constant and that there is a stepless continuity between the regions forming the sealing lips 43, 44 and the ambient constant thickness region of the sealing membrane 41.

The examples given above show that the elastic properties of the sealing lips 43, 44 can be varied, or set, within a wide range in order to facilitate an optimum contact between the sealing lips 43, 44 and medical instrument with a wide spectrum of cross sections and, in particular, diameters. Both sealing membranes abutting on each other can provide similarly or differently designed sealing lips.

The embodiments of sealing membranes 41, 51 illustrated with reference to FIGS. 3 through 7 are substantially plate-shaped and planar. In the following, examples of curved, in particular dome-shaped sealing membranes are illustrated with reference to FIGS. 8 through 17. What is described with reference to FIGS. 3 through 7 applies accordingly for the sealing lips.

Figure 8:
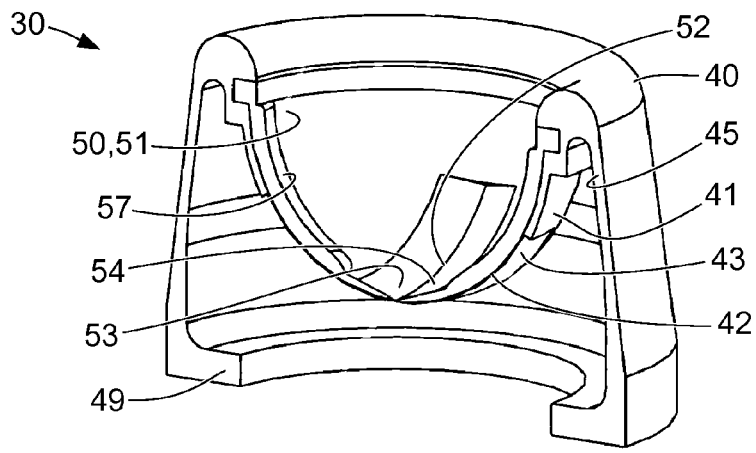
FIG. 8 displays a schematic representation of sealing means.

FIG. 8 displays a schematic axonometric representation of another embodiment of sealing means 30. In FIG. 8, the sealing means 30 is shown in section along a plane comprising the longitudinal axis 28 (confer FIG. 1) of a trocar 20, or rather a trocar's cannula, for which the sealing means 30 is provided.

The sealing means 30 comprises a first, integrally formed sealing membrane component 40 and a second, integrally formed sealing membrane component 50. Each of the first sealing membrane component 40 and the second sealing membrane component 50 comprises silicone or another elastic material. Both sealing membrane components 40, 50 can comprise the same or different materials.

The first sealing membrane component 40 comprises a first sealing membrane 41 with a first slit 42 in the first sealing membrane 40. The first slit 42 of the first sealing membrane 41 lies in the sectional plane. Therefore, only one of the two sealing lips 43 adjoining to the first slit 42 is visible in FIG. 8.

Furthermore, the first sealing membrane component 40 comprises an elastic wall section 45 in the shape of a lateral surface. The elastic wall section 45 in the shape of a lateral surface substantially provides the shape of a section of an envelope of a cone and is positioned ring-like around the first sealing membrane 41 and the second sealing membrane component 50. The elastic wall section 54 connects the outer boundary of the first sealing membrane 41 and an edge profile 49. The edge profile 49 forms an attachment region for a positive-locking connection of the sealing means 30 with a proximal end of a trocar (confer FIGS. 1 and 2), or rather a trocar's cannula.

The second sealing membrane component 50 comprises a second sealing membrane 51 with a second slit 52 between sealing lips 53, 54. The second slit 52 is perpendicular to the first slit 42 in the first sealing membrane 41 and perpendicular to the sectional plane of FIG. 8. Furthermore, the sealing membrane component 50 comprises one reinforcement rib 57 at each side of the second slit 52. The reinforcement ribs 57 are substantially located perpendicular and central to the second slit 52, and each reinforcement rib 57 extends from the outer boundary of the second sealing membrane 51 to the vicinity of the sealing lips 53, 54. As an example, each reinforcement rib 57 provides a semi circular, semi elliptical or rectangular cross section.

The elasticity of the elastic wall section 45 in the shape of a lateral surface facilitates a motion of the sealing membranes 41, 51 relative to the sealing means' 30 attachment region formed by the edge profile 49, in particular a shift perpendicular to the longitudinal axis 28 (confer FIG. 1) and/or tilting or pivoting around axes perpendicular to the longitudinal axis 28.

Figure 9:
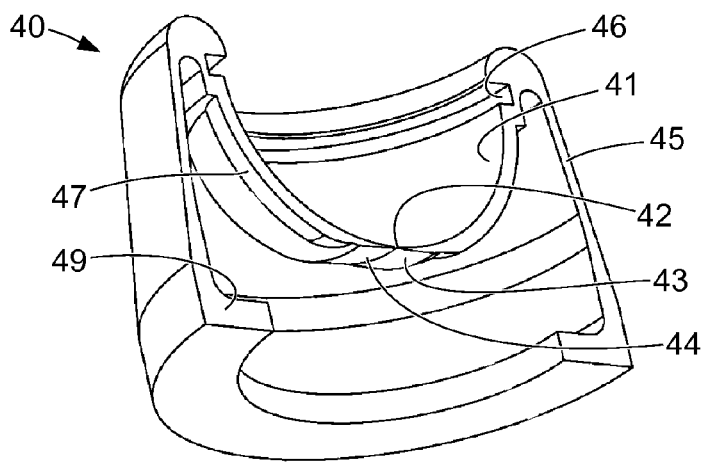
FIG. 9 displays another schematic representation of a first sealing membrane component of FIG. 8.

FIG. 9 displays another schematic axonometric representation of the first sealing membrane component 40 of the embodiment of FIG. 8. Again, in FIG. 9 the first sealing membrane component 40 is cut along a plane comprising the longitudinal axis 28 (confer FIG. 1). However, the sectional plane of FIG. 9 is perpendicular to the sectional plane of FIG. 8 and perpendicular to the first slit 42 in the first sealing membrane 41. Therefore and due to the different viewing direction, both sealing lips 43, 44 forming the first slit 42 are visible.

Furthermore, a pair of reinforcing ribs 47 at the first sealing membrane's 41 side, or rather surface, adverted from the second sealing membrane component 50 are visible. The reinforcement ribs 47 are arranged symmetric, perpendicular and central to the first slit 42. Again, each of the reinforcement ribs 47 at the first sealing membrane component 40 can provide a semi circular, semi elliptic, rectangular cross section and extend from the outer boundary of the first sealing membrane 41 to the vicinity of the sealing lips 43, 44.

Furthermore, a first edge profile 46 at the boundary of the first sealing membrane 41 is visible in FIG. 9. The first edge profile 46 is formed by a circular groove open towards the longitudinal axis.

Figure 10:
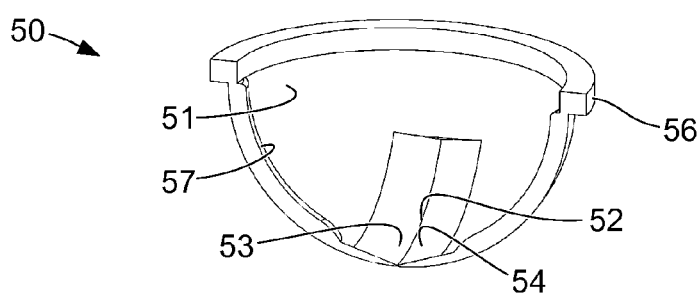
FIG. 10 displays another schematic representation of a second sealing membrane component of FIG. 8.

FIG. 10 displays another schematic axonometric representation of the second sealing membrane component 50 of the embodiment of FIGS. 8 and 9. Again, in FIG. 10, the second sealing membrane component 50 is shown cut along a plane comprising the longitudinal axis 28 (confer FIG. 1). The sectional plane of FIG. 10 corresponds to the sectional plane of FIG. 8 and is perpendicular to the sectional plane of FIG. 9 and to the second slit 52 in the second sealing membrane 51.

The characteristics of the second sealing membrane component 50 described above with reference to FIG. 8 are visible in FIG. 10. Furthermore, a second edge profile 56 at the outer boundary of the second sealing membrane 51, or of the second sealing membrane component 50 is visible. The second edge profile 56 provides the shape of a flange protruding radially outwards. The first edge profile 46 at the first sealing membrane component 40 (confer FIG. 9) and the second edge profile 56 at the second sealing membrane component 50 provide corresponding cross sections.

It is visible in FIG. 8 that the first edge profile 46 at the first sealing membrane component 40 can accommodate the second edge profile 56 at the second sealing membrane component 50. In this way, the edge profiles 46, 56 form a positive-locking connection between the sealing membrane components 40, 50, wherein, due to the elasticity of both sealing membrane components 40, 50, the connection can be established and released repeatedly. For the purpose of releasing the positive-locking connection, in particular for the purpose of extracting the second edge profile 56 from the first edge profile 46, a tap or another facility can be provided at the second sealing membrane component 50, which facility can be grabbed, for instance, with two fingers for extracting the second edge profile 56 from the first edge profile 46.

The first sealing membrane component 40 and the second sealing membrane component 50, in particular the first sealing membrane 41 and the second sealing membrane 51 and the edge profiles 46, 56, are designed such that the sealing membranes 41, 51 entirely abut on each other when the second edge profile 56 is received in the first edge profile 46. In order to guarantee the designated relative orientation of the slits 42, 52 in the sealing membranes 41, 51 the edge profiles 46, 56 are, in particular differing from the representation in FIGS. 8 through 10, not entirely circularly symmetric. Rather, a predetermined relative orientation is defined for instance by means of a projection at one of the sealing membrane components 40, 50 and a corresponding recess at the other sealing membrane component 40, 50.

In the embodiments illustrated with reference to FIGS. 8 through 10, the sealing means 41, 51 are dome-shaped. In particular, each of the inner, or proximal, surface of the first sealing membrane 41 abutting on the second sealing membrane 51 and the outer, or distal, surface of the second sealing membrane 51 abutting on the first sealing membrane 41 is spherical. As alternatives, other shapes are feasible, for instance the shape of a biaxial or triaxial ellipsoid.

The surfaces of the first sealing membrane component 40 and the second sealing membrane component 50 can be partially or entirely comprise a friction reducing coating, for instance Poly (p-Xylylene), also sold under the Trademark Parylene. A friction reducing coating in the region of the sealing lips 43, 44, 53, 54 can reduce static and/or dynamic friction between the sealing means 30 and a medical instrument introduced into the sealing means 30. A friction reducing coating at the first sealing membrane's 41 inner, proximal surface abutting on the second sealing membrane 51 and at the second sealing membrane's 51 outer, distal surface abutting on the first sealing membrane 41 can, in particular, reduce the static friction between the sealing membranes 41, 51 and, thereby, reduce wear and improve the sealing effect.

Figure 11:
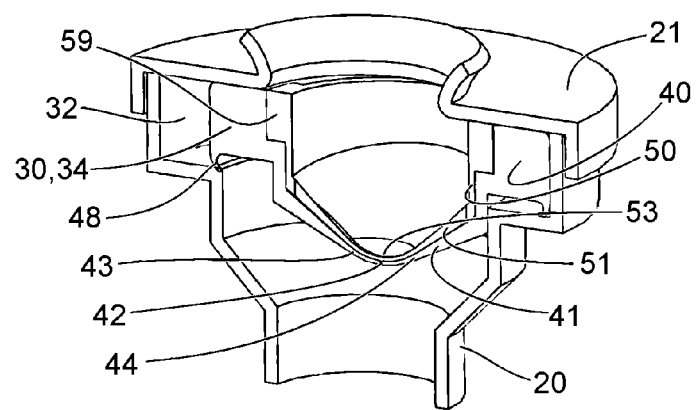
FIG. 11 displays a schematic axonometric representation of another sealing means at an end of a trocar.
Figure 12:
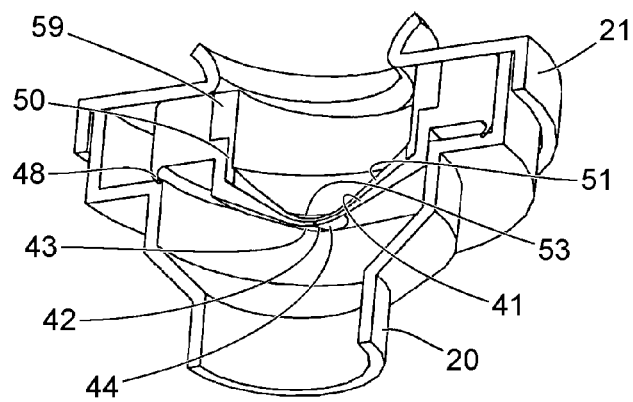
FIG. 12 displays another schematic axonometric representation of the sealing means of FIG. 11.

FIGS. 11 and 12 display schematic axonometric representations of another embodiment of sealing means 30. Similar to the FIGS. 8 through 10, in FIGS. 11 and 12 the sealing means 30 is shown cut along a plane comprising the longitudinal axis 28 (confer FIG. 1). The sectional planes of FIGS. 11 and 12 are identical. Unlike the representations in FIGS. 8 through 10, not only the sealing means 30 but also the proximal end of a trocar 20, or rather a trocar's cannula, is illustrated. The illustrations in FIGS. 11 and 12 merely differ in the viewing direction in which the embodiment is shown. Therefore, all statements below simultaneously refer to both FIGS. 11 and 12.

The proximal end of the trocar 20 comprises a stepped enlargement of its cross section forming, together with a lid 21, a cavity 32 provided for reception of the sealing means 30, or rather a disc-shaped rim 34 of the sealing means 30. The disc-shaped rim 34 and the cavity 32 are complementary such that the sealing means is guided with little or no clearance in the direction parallel to the longitudinal axis 28 (confer FIG. 1) and is provided a predetermined room in the directions perpendicular to the longitudinal axis 28, within which room the sealing means 30 can be shifted. In other words, there is a two dimensional floating mount of the sealing means 30 in the cavity 32 between the stepped enlargement of the trocar 20 and the lid 21. A circular slide seal 48 in fluid tight contact with a corresponding circular surface at the proximal end of the trocar is provided at the disc-shaped rim 34 of the sealing means 30.

Similar to the embodiment illustrated above with reference to FIGS. 8 through 10, the sealing means 30 comprises a first sealing membrane component 40 and a second sealing membrane component 50 each of which comprising silicone or another elastic material. The first sealing membrane component 40 comprises the disc-shaped rim 34 of the sealing means 30 and a first sealing membrane 41 with a first slit 42 between sealing lips 40 perpendicular to the sectional planes of FIGS. 11 and 12. The second sealing membrane component 50 comprises a second sealing membrane 51 with a second slit 52 in the sectional plane of FIGS. 11 and 12 and between a sealing lip 53 and another sealing lip not shown in FIGS. 11 and 12.

The second sealing membrane component 50 is held in the predetermined position shown in FIGS. 11 and 12 relative to the first sealing membrane component 40 by positive-locking with the first sealing membrane component 40 or as an effect of the lid 21. In this relative position of the sealing membrane components 40, 50, the sealing membranes 41, 51 entirely abut on each other, similar to the above description with reference to FIGS. 8 through 10.

A projection 59 at the second sealing membrane component 50 is particularly visible in FIG. 11. The projection 59 is received in a corresponding recess at the first sealing membrane component 40 and forces, by positive-locking, a predetermined relative orientation of the sealing membrane components 40, 50 and, thereby, of the slits 42, 52, too.

The sealing membranes 41, 51 are, in a broader sense, dome-shaped, but not entirely spherically curved. Only in a central region close to the crossing point of the two slits, 41, 52, the membranes 41, 51 are spherically or substantially spherically curved. Adjacent to this central region, a ring-shaped region is provided in which each of the membranes 41, 51 substantially provide the shape of a section of an envelope of a cone. Each of the sealing membranes 41, 51 provides a thickness increasing towards its outer boundary.

The surfaces of the sealing membrane components 40, 50 can partially or entirely provide a friction reducing coating.

The sealing membranes 41, 51 can be moved, in particular shifted, relative to the attachment region, or to a trocar, respectively, due to the elasticity of the elastic wall section 45 in the embodiment of FIGS. 8 through 10 and since the disc-shaped rim 34 of the sealing means 30 can be shifted in the corresponding cavity 32 in the embodiment of FIGS. 11 and 12. Guidance of a medical instrument to be introduced into the sealing means towards the center of the sealing membranes 41, 51 is caused by a dome-shape or, in particular, a substantially spherical design in the embodiments of FIGS. 8 through 10, and by a cone-shaped design of the sealing membranes 41, 51 in the embodiments of FIGS. 11 and 12. The dome-shape or, in particular, the substantially spherical design of the sealing membranes 41, 51 of the embodiment of FIGS. 8 through 10 can also be realized when the sealing means 30 can be shifted according to the embodiment of FIGS. 11 and 12. The other way around, when the sealing membranes 41, 51 can be moved relative to the attachment region 49 due to the elasticity of the wall section 45 shaped like a lateral surface according the embodiment of FIGS. 8 through 10, the sealing membranes 41, 51 can be designed according to the embodiment of FIGS. 11 and 12.

Figure 13:
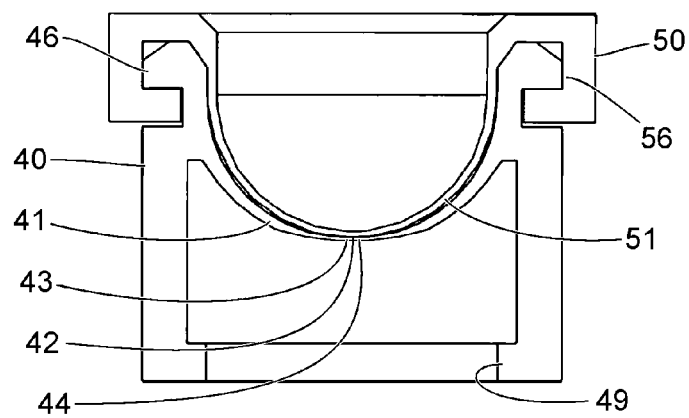
FIG. 13 displays a schematic representation of a section through another sealing means.

FIG. 13 displays a schematic sectional view of another embodiment of sealing means 30. Similar to the embodiment of FIGS. 8 through 10, the sealing means 30 comprises a first sealing membrane component 40 with a first sealing membrane 41 and an edge profile 49 forming an attachment region, and a second sealing membrane component 50 with a second sealing membrane 51. Inter alia, the sealing means 30 differs from the embodiment of FIGS. 8 through 10 in the design of edge profiles 46, 56 at the boundaries of the sealing membranes 41, 51 for a positive-locking connection of the sealing membrane components 40, 50.

Furthermore, the sealing means 30 differs from the embodiment of FIGS. 8 through 10 in the thickness of the sealing membranes 41, 51 continuously increasing from the slits 42, 52 towards the outer boundary. The first slit 42 in the first sealing membrane 41 is perpendicular to the sectional plane of FIG. 13, the increase of the thickness of the first sealing membrane 41 from the first slit 42 towards the boundary of the first sealing membrane 41 is visible. The second slit 52 in the second sealing membrane 51 is in the sectional plane of FIG. 13. Therefore, the second sealing membrane's 51 thickness visible in FIG. 13 directly at the second slit 52 is substantially constant.

Figure 14:
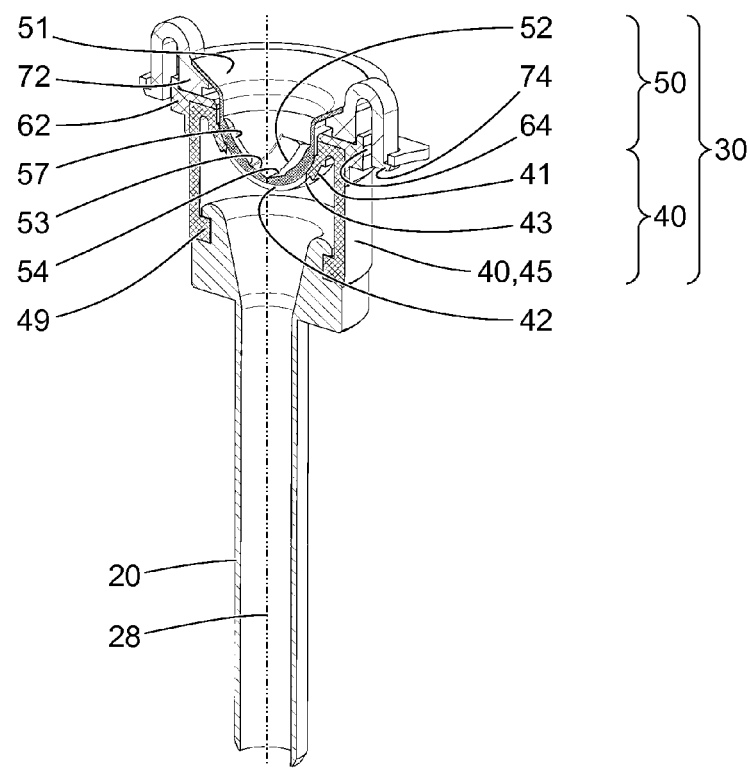
FIG. 14 displays a schematic axonometric sectional representation of another trocar with another sealing means.

FIG. 14 displays a schematic axonometric sectional representation of another trocar 20 with another sealing means 30. The sectional plane comprises the longitudinal axis 28 of the trocar 20 and corresponds in particular to the sectional planes of FIGS. 1, 2, 4, 8, 10, 11, 12, 13.

The trocar 20 is largely similar to the trocar illustrated above with reference to FIGS. 1 and 2. Regarding many features, properties and functions, the sealing means 30 is similar to the sealing means illustrated above with reference to FIGS. 8 through 10, in particular with regard to the dome-shape of the sealing membranes 41, 51, the arrangement of the slits 42, 52 and the shape of the sealing lips 43, 44, 53, 54.

Each of the sealing membranes 41, 51 can provide the shape of an envelope of a cone in an outer, ring-shaped region and a dome-shape, in particular a spherical curvature, in a central region and, in so far, be similar to the sealing means illustrated above with reference to FIGS. 11 and 12. Furthermore, each of the sealing membranes 41, 51 can provide the shape described above with reference to FIG. 13, in so far differing from the illustration in FIG. 14.

Only those features and properties of the sealing means 30 are illustrated below, in which the sealing means 30 differs from the embodiments of FIGS. 8 through 13, in particular from the embodiments of FIGS. 8 through 10.

The first sealing membrane component 40 comprises, in particular, the first sealing membrane 41 and a first frame 62. The second sealing membrane component 50 comprises, in particular, the second sealing membrane 51 and a second frame 72. Each of the first frame 62 and the second frame 72 comprises a material which is considerably stiffer or less elastic than the material or the materials of the sealing membranes 41, 51. The first sealing membrane 41 is bonded to the first frame 62, in particular glued, welded or otherwise materially bonded at a ring-shape surface. As an alternative, the first sealing membrane 41 and the first frame 62 are materially bonded to each other during injection molding or another molding process. The second sealing membrane 51 is bonded to the second frame 72, in particular glued, welded or otherwise materially bonded at a ring-shaped surface. As an alternative, the second sealing membrane 51 and the second frame 72 can be materially bonded to each other during injection molding or another molding process.

As an alternative different from the illustration in FIG. 14, the first sealing membrane 41 and the first frame 62 are formed of the same material and in particular simultaneously and ab initio integrally. The second sealing membrane 51 and the second frame 72 can be formed of the same material and in particular simultaneously and ab initio integrally, too. In these cases, the first frame 62 and the second frame 72 provide a considerably lower elasticity than the first sealing membrane 41 and the second sealing membrane 51 due to a considerably larger material thickness.

Two recess, in particular two holes 64 are provided at the first frame 62 at opposite sides. Two latches 74 are provided at the second frame 72 at opposite sides. U-shaped regions between the frame 72 and the latches 74 are provided as elastic elements and facilitate a movement of the latches 74 when elastic forces are overcome. The holes 64 at the first frame 62 are arranged and configured corresponding to the latches 74 at the second frame 72. With the designated relative arrangement of the sealing membrane components 40, 50 illustrated in FIG. 14, each latch 74 engages a corresponding hole 64 and, together with the hole 64, forms a snap-lock connection. The snap-lock connections between the latches 74 and the holes 64 keep the sealing membrane components 40, 50 in the designated relative arrangement illustrated in FIG. 14.

Figure 15:
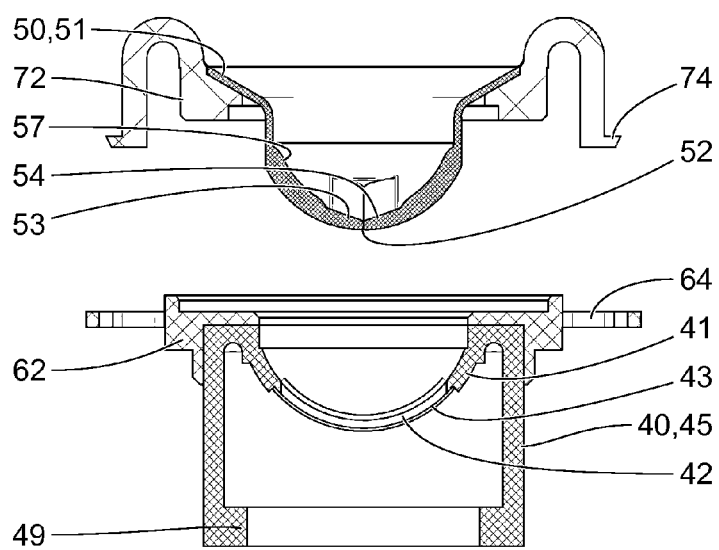
FIG. 15 displays a schematic sectional representation of the sealing means of FIG. 14.

FIG. 15 displays a further schematic sectional representation of the sealing means 30 of FIG. 14. The sectional plane of FIG. 15 comprises the longitudinal axis 28 (confer FIG. 14) and corresponds to the sectional area of FIG. 14. In FIG. 15, the sealing membrane components 40, 50 are shown mechanically disconnected and spaced apart from each other. The first sealing membrane component 40 is displayed in the lower part of FIG. 15, the second sealing membrane component 50 is displayed in the upper part of FIG. 15.

Figure 16:
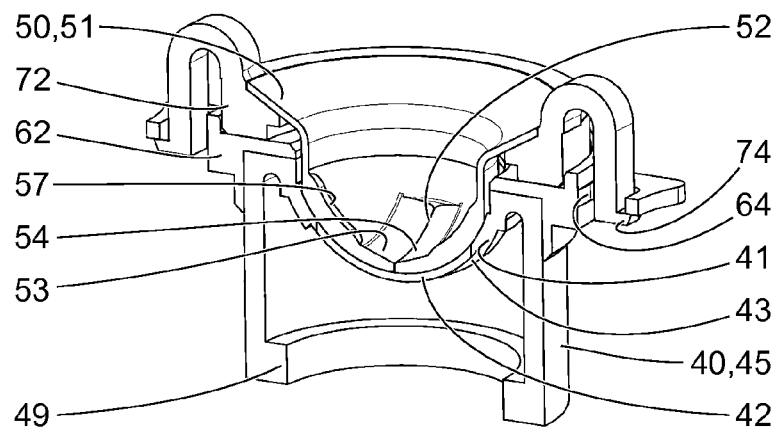
FIG. 16 displays another schematic axonometric sectional representation of the sealing means of FIGS. 14 and 15.
Figure 17:
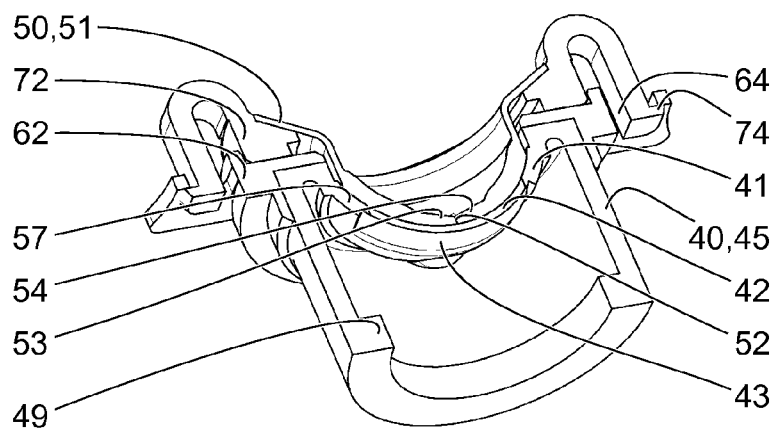
FIG. 17 displays another schematic axonometric section representation of the sealing means of FIGS. 14 through 16.

FIGS. 16 and 17 display further schematic axonometric sectional representations of the sealing means 30 of FIGS. 14 and 15. The sectional planes of FIGS. 16 and 17 comprise the longitudinal axis 28 (confer FIG. 14) and correspond to the sectional planes of FIGS. 14 and 15. The sealing membrane components 40, 50 are shown in their designated relative arrangement and mechanically connected with each other, similar to the representation in FIG. 14.

Starting from the configuration, or situation shown in FIGS. 14, 16 and 17 the snap-lock connections can be released by manual application of a force to the latches 74. Thereafter, the sealing membrane components 40, 50 can be separated from each other and, subsequently, disposed or cleaned and sterilized. After cleaning or after sterilizing, the sealing membrane components 40, 50 can be mechanically reconnected with each other by reestablishing the snap-lock connection.

Contrary to the representations with reference to FIGS. 14 through 17, a different number of latches 74 and holes 64 and a different, corresponding number of snap-lock connections between the sealing membrane components 40, 50 can be provided. In particular, three or four holes 64, latches 74 and snap-lock connections are provided.

What is claimed is:

1. A sealing means for sealing of an introduction facility for a medical instrument, the sealing means comprising:
    a first sealing membrane of an elastic material, the first sealing membrane having an annular first edge profile at least partially defining an outer boundary of the first sealing membrane, and a dome-shaped region extending between the first edge profile, the dome-shaped region having a first slit extending therethrough; and
    a second sealing membrane of an elastic material, the second sealing membrane having an annular second edge profile at least partially defining an outer boundary, of the second sealing membrane, and a dome-shaped region extending between the second edge profile, the dome-shaped region having a second slit extending therethrough;
    the first sealing membrane and the second sealing membrane laminarily abutting on each other;
    the first sealing membrane and the second sealing membrane being arranged such that the first slit and the second slit are not parallel with each other, and each of the first slit and the second slit being unbranched.

2. The sealing means according to claim 1, wherein at least one of a thickness of the dome-shaped region of the first sealing membrane continuously or discontinuously decreases towards the first slit, a thickness of the dome-shaped region of the second sealing membrane continuously or discontinuously decreases towards the second slit.

3. The sealing means according to claim 1, wherein at least one of (i) in areas of the dome-shaped region of the first sealing membrane adjacent to both sides of the first slit, a thickness of the first sealing membrane decreases in wedge-shape towards the first slit, and (ii) in areas of the dome-shaped region of the second sealing membrane adjacent to both sides of the second slit, a thickness of the second sealing membrane decreases in wedge-shape towards the second slit.

4. The sealing means according to claim 1, wherein each of a length of the first slit and a length of the second slit is at least twice a largest diameter of a region of a medical instrument for which the sealing means is provided.

5. The sealing means according to claim 1, wherein each of the first sealing membrane and the second sealing membrane is configured such that a sealing lip adjacent to each slit abuts on the largest circular cross section of a medical instrument for which the sealing means is provided in a region extending, in circumferential direction, over at least 90 degrees.

6. The sealing means according to claim 1, wherein the first sealing membrane and the second sealing membrane are mechanically connected to each other by one or more snap-lock connections.

7. The sealing means according to claim 1, wherein each of the first slit and the second slit is straight.

8. The sealing means according to claim 1, wherein the dome-shaped regions of each of the first sealing membrane and the second sealing membrane comprises a spherical surface region adjacent to the first slit and the second slit, respectively.

9. The sealing means according to claim 1, wherein the first edge profile and the second edge profile are configured to provide a positive-locking connection of the first sealing membrane and the second sealing membrane.

10. The sealing means according to claim 1, wherein both the outer boundary of the first sealing membrane and the outer boundary of the second sealing membrane are offset, at at least one respective position, from circular symmetry relative to one another, such that a predetermined relative orientation of the first sealing membrane and the second sealing membrane is given.

11. The sealing means according to claim 1, further comprising at least one of a reinforcement rib at the first sealing membrane and a reinforcement rib at the second sealing membrane.

12. The sealing means according to claim 1, wherein at least one of the first sealing membrane and the second sealing membrane provides a friction reducing coating at at least one side thereof.

13. The sealing means according to claim 1, further comprising:
    an attachment region configured to permit attachment of the sealing means to a trocar or to another medical device; and
    an elastic wall section connecting the second sealing membrane to the attachment region, wherein an elasticity of the elastic wall section facilitates a motion of the first and second sealing membranes relative to the attachment region.

14. A trocar with the sealing means according to claim 1.

15. The sealing means according to claim 1, wherein each of the first slit and the second slit is arcuate with a curvature radius at least as large as a length, a width, or a diameter of the first sealing membrane and the second sealing membrane, respectively.

* * * * *